United States Patent [19]

Dombrowski et al.

[11] Patent Number: 5,399,582

[45] Date of Patent: Mar. 21, 1995

[54] ANTIPARASITIC AGENTS

[75] Inventors: Anne W. Dombrowski, East Brunswick; Richard G. Endris, Martinsville; Gregory L. Helms, Fanwood; Otto D. Hensens, Red Bank; John G. Ondeyka, Fanwood; Dan A. Ostlind, Watchung; Jon D. Polishook, Scotch Plains; Deborah L. Zink, Manalapan, all of N.J.

[73] Assignee: Merck & Co., Inc., Rahway, N.J.

[21] Appl. No.: 146,638

[22] Filed: Nov. 1, 1993

[51] Int. Cl.⁶ ............... C07D 491/12; C07D 491/22; A01N 43/90
[52] U.S. Cl. ..................................... 514/410; 548/417
[58] Field of Search ......................... 548/417; 514/410

[56] References Cited

U.S. PATENT DOCUMENTS 4,199,569  4/1980  Chabala et al. ............... 536/7.1 X
4,310,519  1/1982  Albers-Schonberg et al. .... 549/264 X

OTHER PUBLICATIONS

Washington Agri. Exp. Station. Tech. Bulletin 71, Mar. 1972, by S. C. Jong, et al., entitled "Illustrations & Descriptions of Conodial States of some Hypoxylon species", pp. 1 to 51.

Methods for Research on Soilborne Phytopathogenic Fungi, No. 71, p. 247, (1992).

Can, J. Bot., vol. 69, pp. 1477–1482 (1991), Bills, et al., entitled "Microfungi from *Carpinus caroliniana*".

J. Chem. Soc. Perkin Trans. 1, 1984, pp. 697–701, deJesus, et al., entitled "Structure Elucidation of the Janthitrems, Novel Tremorgenic Mycotoxins from *Penicillium janthinellum*".

*Primary Examiner*—Joseph Paul Brust
*Attorney, Agent, or Firm*—David L. Rose; Joseph F. DiPrima

[57] ABSTRACT

There are disclosed novel compounds which are derived from the fermentation of a strain of Nodulisporium sp. The compounds are highly potent ectoparasiticidal, antiparasitic and, insecticidal gents.

2 Claims, 3 Drawing Sheets

ANTIPARASITIC AGENTS

BACKGROUND OF THE INVENTION

Novel antiparasitic agents are well known such as the avermectins disclosed in U.S. Pat. Nos. 4,310,519 and 4,199,569. However, such avermectin compounds, while potent agents against internal and external parasites, are structurally very significantly different from the instant compounds. The avermectins, being macrocyclic agents isolated from an actinomycete, are not related to the instant polycyclic fungal metabolites. In de Jesus et al., *J. Chem Soc. Perkin Trans I*, pg 697–701 (1984) are described fungal metabolites identified as janthitrems with a polycyclic structure which, however, lacks several structural elements of the instant compounds.

SUMMARY OF THE INVENTION

The instant invention is concerned with the preparation of novel antiparasitic agents and ectoparasiticidal agents. Thus it is an object of this invention to disclose such novel compounds. A further object is to provide a novel method for the preparation of such compounds. A further object is to describe the microorganism used to prepare such compounds and the fermentation conditions applicable to such production. A still further object is to describe compositions and methods using the instant compounds as antiparasitic agents. Further objects will become apparent from reading the following description.

BRIEF DESCRIPTION OF THE DRAWING

FIG. 1 is a nuclear magnetic resonance spectra of Compound 1 recorded at 500 MHz in $CD_2Cl_2$ on a Varian Unity 500 NMR spectrometer at 25° C. Chemical shifts are indicated in ppu relative to TMS at zero ppu using the solvent peak at $\delta$ 5.32 as an internal standard. Only diagnostic peaks are noted.

FIG. 2 is a nuclear magnetic resonance spectrum of Compound 2 recorded at 400 MHz in $CD_2Cl_2$ on a Varian Unity 400 NMR spectrometer at 25° C. Chemical shifts are indicated in ppu relative to TMS at zero ppu using the solvent peak at $\delta$ 5.32 as an internal standard. Only diagnostic peaks are noted.

FIG. 3 is a nuclear magnetic resonance spectrum of Compound 3 recorded at 300 MHz in $CDCl_3$ on a Varian XL300 NMR spectrometer at ambient temperature. Chemical shifts are indicated in ppu relative to TMS at zero ppu using the solvent peak at $\delta$ 7.24 as an internal standard. Only diagnostic peaks are rated.

DETAILED DESCRIPTION OF THE INVENTION

Figure 1:
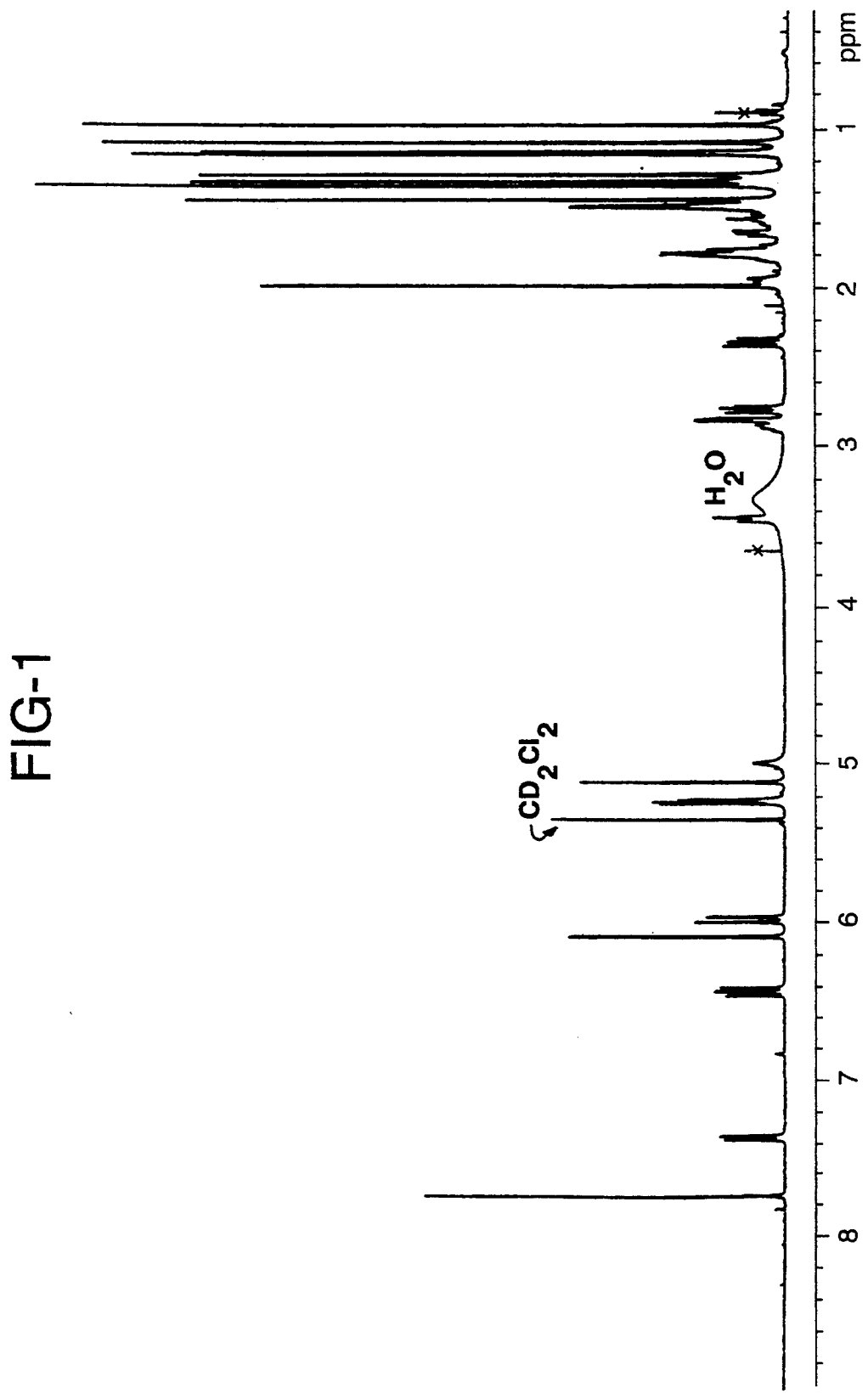
FIGS. 1, 2 and 3 are proton nuclear negtative resonance spectra of Compounds 1, 2 and 3 respectively. In the figures, several of the resonance peaks are marked with an "X". These peaks are the result of the presence of solvent and are not significant to the structure of the compounds.

The present invention is concerned with novel compounds of a unique structure. This invention also concerns a novel process for making the instant compounds in a fermentation medium of Nodulisporium sp. or a mutant thereof.

The compounds of the instant invention have the following structures:

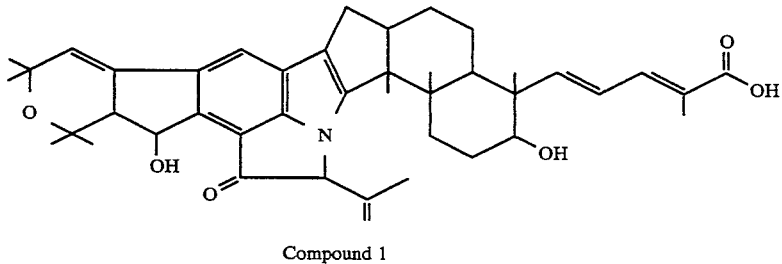

Compound 1

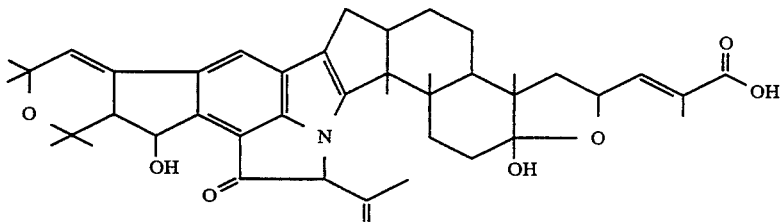

Compound 2

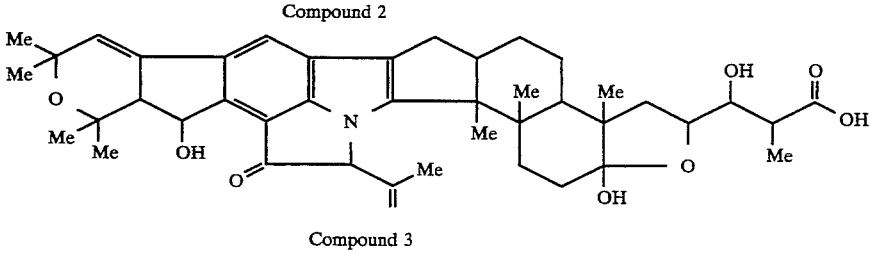

Compound 3

The above structural formulae are shown without a definitive stereochemistry at certain positions and with a defined stereochemistry at other positions and the instant invention should be construed as encompassing all such stereoisomers. In particular, the stereoisomers at the various asymetric centers may be oriented either α- or β- representing such groups being below or above the general plane of the molecule, respectively.

The compounds of this invention finds their primary use as antiparasitic agents in the treatment and/or prevention and treatment of diseases caused by parasites, for example, arthropod parasites such as ticks, lice, fleas, and other biting insects in domesticated animals and poultry, such as Tenophalides, Ixodes, Psoroptes, Lucilia and Hemotobia. They are also effective in treatment of parasitic diseases that occur in other animals including humans. The optimum amount to be employed for best results will, of course, depend upon the species of animal to be treated and the type and severity of parasitic infection or infestation. Generally, good results are obtained with our novel compound by the oral administration of from about 0.001 to about 100 mg per kg of animal body weight, such total dose being given at one time or in divided doses over a relatively short period of time such as 1–5 days. With the novel compound of the present invention, excellent control of such parasites is obtained in animals by administering from about 0.025 to about 50 mg per kg of body weight in a single dose. Repeat treatments are given where required to combat re-infections and are dependent upon the species of parasite and the husbandry techniques being employed. The techniques for administering these materials to animals are known to those skilled in the veterinary field.

The instant compound is also active against household pests such as the cockroach, Blatella sp., ants, Solenopsis clothes moth, Tineola sp., carpet beetle, Attagenus sp. and the housefly *Musca domestica*.

The compound of the present invention is also useful against insect pests of stored grains such as Tribolium sp., Tenebrio sp. and of agricultural plants such as spider mites, (Tetranychus sp.), aphids, Acyrthiosiphon migratory orthopterans such as locusts and immature stages of insects living on plant tissue. The compounds are useful as nematocides for the control of soil nematodes and plant parasites such as Meloidogyne sp. which may be of importance in agriculture.

The instant compounds can be administered orally in a unit dosage form such as a capsule, bolus or tablet, or as a liquid drench that is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to about 1.0% by weight of the active compounds. Preferred drench formulations may contain from about 0.01 to about 0.1% by weight. The capsules and boluses comprise the active ingredient admixed with a carrier vehicle such as starch, talc, magnesium stearate, or dicalcium phosphate.

Where it is desired to administer the compounds of the present invention in a dry, solid unit dosage form, capsules, boluses or tablets containing the desired amount of the instant compounds usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the compounds of the present invention is to be administered via an animal feedstuff, they are intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol, formal and aqueous parenteral formulations are also used. The compounds of the present invention are dissolved or suspended in the parenteral formulation for administration; such formulations generally contain from about 0.55% to about 5% by weight of the instant compound.

When the compounds described herein are administered as components of the feed of the animals, or dissolved or suspended in the drinking water, compositions are provided in which the active compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the instant compounds are present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The compounds of the present invention are intimately dispersed throughout the carrier by methods such as grinding, stirring, milling or tumbling. Compositions containing from about 0.005% to about 2.0% by weight of the instant compound are particularly suitable as feed premixes. Feed supplements, which are fed directly to the animal, contain from about 0.0002% to about 0.3% by weight of the instant compound.

Such supplements are added to the animal feed in an amount to give the finished feed the concentration of active compound desired for the treatment and control of parasitic diseases. Although the desired concentration of the compounds of the present invention will vary depending upon the factors previously mentioned as well as upon the particular compound employed, the compounds of this invention are usually fed at concentrations of between about 0.001% to about 0.2% in the feed in order to achieve the desired antiparasitic result.

In addition, where the compound is to be added to an animal's feed, it is possible to utilize the dried mycelial cake from the fermentation broth. The mycelia contain a preponderance of the activity and since the level of the activity of the mycelia can be determined, it can be added directly to the animal's feed.

The compounds of this invention also are useful in combating agricultural pests that inflict damage upon crops while they are growing or while in storage. The compound is applied using known techniques as sprays, dusts, emulsions and the like, to the growing or stored crops to effect protection from such agricultural pests.

The antiparasitic activity of the instant compounds may be determined by orally administering via the feed, a sample of the individual compound, a mixture of such compounds, a concentrated extract, and the like to a mouse which had been infected 3 days earlier with an appropriate parasite. At 11, 12 and 13 days after the initiation of the medication, the feces of the mouse are examined for eggs, and on the next day the mouse is sacrificed and the number of worms present in the proximal portion of the small intestine are determined. An active compound is observed when there is a significant reduction of egg and worm counts when compared to infected, unmedicated controls.

The novel compounds of the instant invention are prepared by the fermentation of a strain of the fungal genus Nodulisporium. One such culture, is designated MF-5954 in the culture collection of Merck & Co., Inc., Rahway, N.J. A producing strain of MF- 5954 has been deposited in the permanent collection of the American Type Culture Collection at 12301 Parklawn Drive, Rockville, Md. 20852, and has been given the accession number 74245. The deposit was made on 21 Sep. 1993 under The Budapest Treaty on the International Recognition of the Deposit of Microorganisms for the Purposes of Patent Procedure.

The morphological and cultural charactaristics of Nodulisporium sp MF-5954, are as follows:

MF-5954 (produces L-954,967) was isolated as JP337, an endophytic fungus from woody plant tissue by the surface sterilization method of Bills and Polishook (1991). In the following description, capitalized color names are from Ridgway (1912).

On cornmeal agar (Difco) colony attaining a diameter of 42 mm after 6 days at 25° C., 50% relative humidity and 12 hr fluorescent light photoperiod. Colony mat growing submerged, with surface appressed to felty, uncolored throughout; exudate and soluble pigment absent; reverse uncolored; sweet aromatic odor present.

On oatmeal agar (Difco) colony attaining a diameter of 42 mm after 6 days under the same conditions. Colony mat appressed to sparsely cottony, colony center yellow-brown (Mars Yellow, Raw Sienna) to a light yellow-brown (Light Orange Yellow, Antimony Yellow) midway to the margin; margin entire, white; exudate, odor and soluble pigment absent; reverse light brown.

On potato-sucrose agar (Singleton, et. al, 1992) colony attaining a diameter of 43 mm after 6 days under the same conditions. Colony mat appressed to sparsely cottony, reddish brown (Light Russet-Vinaceous) at colony center fading to hyaline at margin, margin indistinct; exudate, odor and soluble pigment absent; reverse red brown (Dark Vinaceous).

At 37° C., on cornmeal agar and in the dark, colony attaining a diameter of 82 mm after 6 days; colony mat cottony throughout except at inoculation point where the mat is appressed, white; margin entire, white; exudate and soluble pigment absent; reverse uncolored; sweet aromatic odor present.

Hyphae hyaline to light brown, septate, with walls smooth to slightly roughened, thick-walled, 2.5–3.5 µm wide. Conidiophores mononematous, erect, 150–400×3.0–4.0 µm, penicillately branched, hyaline to light brown, septate, thick-walled, smooth to finely roughened to verrucose, sometimes with olivaceous, rounded projections (2.5 µm diameter). Conidiogenous cells holoblastic, terminal, 16–24×1.5–2.0 µm, finely roughened to verrucose, cylindrical, irregular at the apex. Conidia obovate to oblong-elliptical with a truncate attachment point, 4.1–5.7×1.6–2.5 µm, hyaline, aseptate, thin-walled, produced sympodially from the apex of the conidiogenous cell, accumulating as a apical cluster on denticals.

MF-5954 is placed in the fungal genus Nodulisporium (Hyphomycetes, Deuteromycotina). The key taxonomic characteristics of this genus include mononematous conidiophores that are typically branched and a sympodulous production of conidia. In addition, the conidial bearing areas are terminal or intercalary and nodulose due to copious conidial production (Jong and Rogers, 1972). These characters distinguish the genus Nodulisporium from other similar fungi, such as Geniculosporium, Xylocladium and Ustilina. These genera are the asexual (anamorph) state of many xylariaceous (Ascomycotina) fungi, such as Hypoxylon, Xylaria, Rosellinia, etc.

Unlike most isolates of Nodulisporium, MF-5954 grows well at 37° C., but does not exhibit any other distinguishing characters in culture to associate it with a known species. Therefore, it is designated as Nodulisporium sp.

Literature Cited

1. Bills, G. F. and Polishook, J. D. 1991. Microfungi from *Carpinus caroliniana*. Can. J. Bot. 69 (7): 1477–1482.
2. Jong, S. C. and Rogers, J. D. 1972. Illustrations and descriptions of conidial states of some Hypoxylon species. Wash. State Agric. Exp. Sta. Tech. Bull. No. 71. 51 p.
3. Ridgway, R. 1912. Color standards and color nomenclature. Publ. by the author, Washington, D.C. 43 p.+53 pl.
4. Singleton, L. L, Mihail, J. D. and Rush, C. M.(Eds). 1992. Methods for research on soilborne phytopathogenic fungi, appendix A, p.247. APS Press, St. Paul, Minn.

The instant compounds are produced during the aerobic fermentation of suitable solid or aqueous nutrient media under conditions described hereinafter, with a producing strain of Nodulisporium sp. Aqueous and solid media such as those used for the production of many antibiotic substances are suitable for use in the process for the production of these polycyclic compounds.

Such nutrient media contain sources of carbon and nitrogen assimilable by the microorganism and generally low levels of inorganic salts. In addition, the fermentation media may contain traces of metals necessary for the growth of the microorganisms, and production of the desired compounds. These are usually present in sufficient concentrations in the complex sources of carbon and nitrogen, which may be used as nutrient sources, but can, of course, be added separately to the medium if desired.

In general, carbohydrates such as sugars, for example glucose, sucrose, maltose, lactose, dextrin, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount of carbohydrate between 1 and 150 g/l in the medium is satisfactory. These carbon sources can be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, distillers solubles, cottonseed meal, meat extract and the like, are readily assimilable by Nodulisporium sp. in the production of the instant compounds. The various sources of nitrogen can be used alone or in combination in amounts ranging from 1 to 5 g/l in the medium.

Among the nutrient inorganic salts which can be incorporated in the culture media are the customary salts capable of yielding sodium, potassium, magnesium, ammonium, calcium, phosphate, sulfate, chloride, carbonate, and like ions. Also included are trace metals such as iron, zinc, manganese, copper, boron, molybdenum and the like.

It should be noted that the media described hereinbelow and in the Examples are merely illustrative of the wide variety of media, which may be employed, and are not intended to be limiting.

The following are examples of media suitable for growing strains of Nodulisporium sp MF-5954, ATCC 74245:

| COMPOSITION OF SLANT MEDIUM | |
| --- | --- |
| Yeast Extract | 4 g |
| Malt Extract | 10 g |
| Glucose | 4 g |
| Bacto Agar | 20 g |
| Distilled Water | 1000 ml |
| pH 7.0 | |

| COMPOSITION OF SEED AND PRODUCTION MEDIA | |
| --- | --- |
| Seed Medium | |
| Component | g/L |
| Yeast extract | 4.0 |
| Malt extract | 8.0 |
| Glucose | 4.0 |
| Junlon | 1.5 |

The medium was prepared with distilled water, the pH adjusted to 7.0 prior to sterilization, and dispensed at 50 ml per 250 ml unbaffled Erlenmeyer flask. Cotton closures were used. Sterilization was at 121° C. for 20 minutes.

PRODUCTION MEDIUM A

1. Solid Portion

Add 1250 cc vermiculite to a 4 L roller bottle. Plug with latex closure; autoclave for 60 min., plus 30 min. dry.

2. Liquid Portion

| Component | g/L |
| --- | --- |
| Glucose | 150.0 |
| Urea | 4.0 |
| N Z amine type A | 4.0 |
| $K_2HPO_4$ | 0.5 |
| $MgSO_4 \cdot 7H_2O$ | 0.25 |
| KCl | 0.25 |
| $ZnSO_4 \cdot 7H_2O$ | 0.9 |
| $CaCO_3$ | 16.5 |

The medium was prepared with distilled water (no pH adjustment). It was dispensed at 425 ml/1 L Erlenmeyer flask. Cotton closures were used, and the medium was sterilized at 121° C. for 15 minutes.

| Production Medium B | |
| --- | --- |
| Component | (g/l) |
| Glycerol | 75.0 |
| Glucose | 10.0 |
| Ardamine PH | 5.0 |
| $(NH_4)_2SO_4$ | 2.0 |
| Soybean meal | 5.0 |
| Tomato paste | 5.0 |
| Sodium citrate | 2.0 |

The medium was prepared with distilled water, pH to 7.0 prior to sterilization. The medium was dispensed at 50 ml per 250 ml unbaffled Erlenmeyer flask. The flasks were closed with cotton and autoclaved at 121° C. for 20 minutes.

The fermentation employing Nodulisporium sp. can be conducted at temperatures ranging from about 20° C. to about 40° C. For optimum results, it is most convenient to conduct these fermentations at a temperature in the range of from about 22° C. to about 36° C. Temperatures of from about 22° C. to about 27° C. are most preferred. The pH of the nutrient medium .suitable for producing the instant compounds can vary from about 6.5 to about 8.0 with a preferred range of from about 6.8 to about 7.3.

Small scale fermentations are conveniently carried out by placing suitable quantities of the nutrient medium in a flask employing known sterile techniques, inoculating the flask with either spores or vegetative cellular growth of Nodulisporium sp., loosely stoppering the flask with cotton and permitting the fermentation to proceed in a constant room temperature of about 25° C. on a rotary shaker at from 95 to 300 rpm for about 7 to 35 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of Nodulisporium sp. The fermentation is allowed to continue for from 7 to 25 days while agitating and/or aerating the nutrient medium at a temperature in the range of from about 22° to 27° C. The degree of aeration is dependent upon several factors such as the size of the fermentor, agitation speed, and the like. Generally the larger scale fermentations are agitated at about 95 to 300 rpm and about 50 to 500 liters per minute (LPM) of air.

The separation of the instant compounds from the whole fermentation broth and the recovery of the compound is carried out by solvent extraction and application of chromatographic fractionations with various chromatographic techniques and solvent systems.

The instant compounds have slight solubility in water, but are soluble in organic solvents. This property conveniently may be employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform and the like. Generally several extractions are desirable to achieve maximum recovery. The solvent removes the instant compounds as well as other substances lacking the antiparasitic activity of the instant compound. If the solvent is a water immiscible one, the layers are separated and the organic solvent is concentrated under reduced pressure. The residue is placed onto a chromatography column preferably containing silica gel. The column retains the desired product and some impurities, but lets many of the impurities, particularly the nonpolar impurities, pass through. The column is washed with a moderately polar organic solvent such as methylene chloride or chloroform to further remove impurities, and is then washed with a mixture of methylene chloride or chloroform and an organic solvent of which acetone, methanol, and ethanol and the like are preferred. The solvent is evaporated and the residue further chromatographed using column chromatography, thin layer chromatography, preparative thin layer chromatography, high pressure liquid chromatography and the like, with silica gel, aluminum oxide, ion exchange resins, dextran gels and the like, as the chromatographic medium, with various solvents and combinations of solvents as the eluent. Thin layer, high pressure, liquid and preparative layer chromatography may be employed to detect the presence of, and to isolate the instant compound.

The use of the foregoing techniques as well as others known to those skilled in the art will afford purified compositions containing the instant compound. The presence of the desired compound is determined by analyzing the various chromatographic fractions for biological activity or physico-chemical characteristics. Both compounds have been determined by detailed analysis of the various spectral characteristics of the compounds, in particular their nuclear magnetic resonance, mass, ultraviolet and infrared spectra.

EXAMPLE 1

1. CULTURE: MF-5954 was received on an agar slant, and was used to prepare FVMs (frozen vegetative mycelia). A portion of the agar slant was aseptically transferred to seed medium A (50 ml/250 ml unbaffled flask). This was incubated on a 2-inch throw gyratory shaker, 220 rpm for 3 days at 25° C., 85% relative humidity (rh), to obtain biomass. Portions of the biomass were transferred into sterile vials containing glycerol and frozen (as FVM). These were maintained in a final concentration of 10-15% glycerol at −75° C. Secondary FVMs were prepared from a primary FVM by transferring 1.0 ml of the thawed primary FVM into seed medium and incubating 2-3 days at 25° C., 220 rpm and freezing as above.

2. SEED: A frozen vial (FVM) was thawed to room temperature and used to inoculate seed cultures of MF-5954 with 0.5-1.0 ml per 50 ml seed medium A. These were grown on a gyratory shaker (220 rpm) for 2-3 days at 25° C., 85% rh. Sometimes a second stage seed was used. To develop this, 1 ml of the first stage seed described above, was diluted into 50 ml fresh seed medium A and incubated 24-30 hrs at 25° C., 220 rpm, 85% rh.

3. PRODUCTION: The composition of production medium A, is a solid substrate fermentation medium. An aliquot (18-24 ml) of the seed was placed into 425 ml of production Medium A. This flask was swirled vigorously to disperse the biomass. The contents were dispensed by pouring into a 4 L roller culture vessel which contained 1250 cubic centimeters of large-particle vermiculite. The contents of the roller bottle were shaken/mixed to insure homogeneous inoculation and coverage. The roller bottles were incubated horizontally, revolving at approximately 4 rpm on a Wheaton roller apparatus, at 22°-25° C., 50-75% rh for 19-28 days, to obtain a secondary metabolite in the fermentation medium.

A number of liquid media were examined for production of the instant compounds, so that the fermentation could be more easily scaled up to large vessels. Production was detected in only a small number of the liquid media tested. A liquid production medium B was used. Seed cultures were inoculated as described above and grown at 220 rpm on a gyratory shaker for 3 days at 25° C. 85% rh. An aliquot of the seed (1 ml) was used to inoculate each production flask, containing 50 ml (2% inoculum). Flasks were incubated on a gyratory shaker (220 rpm) for 21-28 days at 25° C. 50% rh.

The two production methods were essentially equivalent in the amount of product made. However, the second method (liquid production medium B) has the advantage in that it can be scaled up to stirred vessels, so that large quantities can be made. The solid production method (roller bottles of Medium A) makes scale-up difficult.

Production

Larger vessels (22 L tanks) have also been used to produce the instant compounds from this culture.

EXAMPLE 2

Purification and Preliminary Characterization

Twelve 2-liter roller bottles containing the culture grown on media for 21 days were extracted with 650 ml of methyl ethyl ketone (MEK) each for four hours on a rolling machine at 100 rpm. The extracts were filtered and combined and evaporated to dryness under vacuum to a weight of 8 grams. This material was dissolved in 20 ml methylene chloride and charged to a 800 ml silica gel (E. Merck) column in 95:5, methylene chloride:methanol. One column volume each of the following solvents used for elution: 95:5, 9:1, 3:1, 1:1 methylene chloride: methanol and methanol. 40 ml cuts were collected with most of the activity in cuts 51-55 as determined by bioassay (Lucilia). The cuts were combined and evaporated to dryness under vacuum and had a weight of 200 mg. This sample was dissolved in 8.5 ml methanol and charged to a Sephadex LH20 column (Pharmacia) in methanol and 13 ml cuts collected at a flow rate of 6.5 ml/min. Activity was determined to be in cuts 41-50 and these cuts were pooled and dried and had a weight of 90 mg. This material was dissolved in 0.5 ml methanol and two injections made on an Eka Nobel C-18 HPLC column (9.6mm×250 mm) at room temperature monitored at 270 nm with a flow rate of 4 ml/min. The solvent system used was 70:30, acetonitrile:water with 0.1% TFA and active material was isolated in cuts 26-27 in the first isolation and 27-28 in the second. Purity of the compound was verified by analytical HPLC: Eka-Nobel column (4.6×250 mm C-18) at a flow rate of 1 ml/min and 40° C. as well as by TLC in several solvent systems. Pooled cuts were concentrated under vacuum and extracted into methylene chloride, dried, yielding 4.8 mg of pure compound (Compound 1).

Later fractions from the silica column above were also bioactive; they were combined and taken to dryness under vacuum and had a weight of 1.4 g. The solid was washed with methanol several times and contained components with similar UV spectra to that for Compound 1. This spectroscopic property was used to monitor further purification steps and bioactivity was ultimately verified on the pure compounds. Thus, the methanol solution containg 500 mg by weight was fractionated on a 250 ml Sephadex LH-20 column in methanol. The majority of weight was contained in these combined fractions. The material was dried and redissolved in 3 ml methanol and 1 ml injections made on a preparative Zorbax C-18 column (22.5 mm×250 mm) at room temperature using an 80-20, acetonitrile-water (0.1% TFA) solvent system at a flow rate of 8 ml/min with UV detection at 270 nm and collection of 8 ml fractions. Cut 29 from each of the three fractionations were combined to give compound 2 and cuts 21–22 contained compound 3. Both solutions were concentrated and extracted with ethyl acetate, washed with water and dried. Compound 2 had a weight of 1.8 mg and compound 3 was 1.0 mg. Both compounds were characterized as analogs of compound 1 by NMR and MS studies.

Fast Atom Bombardment, (FAB) mass spectra were recorded on a JEOL HX110 mass spectrometer. The FAB spectrum was obtained using a matrix of dithiothreitol:dithioerythritol (20/80). The exact mass measurements were made at high resolution with ultramark 1960 (Fomblin) as the reference compound. Critical high resolution data is indicated below.

| Found | Calculated | Formula | Assignment |
| --- | --- | --- | --- |
| Compound 1 | | | |
| 680.3891 | 680.3951 | $C_{43}H_{53}NO_6+H$ | M+H |
| 662.3790 | 662.3845 | $C_{43}H_{51}NO_5+H$ | 680-$H_2O$ |
| Compound 2 | | | |
| 695.3806 | 695.3822 | $C_{43}H_{53}NO_7$ | $M^+$ |

$^{13}C$ NMR Data $^{13}C$ NMR spectra were recorded in $CD_2Cl_2$ at 100 and 125 MHz on Varian Unity 400 and 500 NMR spectrometers, respectively, at 25° C. Chemical shifts are given in ppm relative to tetramethylsilane (TMS) at zero ppm using the solvent peak at 53.8 ppm as internal standard.

Compound 1 (125 MHz): 198.0, 172.6, 162.0, 154.7, 154.6, 140.8, 140.0, 138.4, 135.9, 134.0, 125.9, 125.1, 122.7, 122.0, 121.8, 117.5*, 116.7, 113.1, 76.8, 76.4*, 75.3, 73.9, 72.6, 58.2, 56.1, 48.0, 47.8, 45.2, 39.1, 32.3, 32.0, 30.1, 29.9, 27.8, 26.0, 25.7, 24.7, 23.5, 19.6, 18.1*, 15.1, 12.6, 11.2 ppm.

The carbon count of 43 is in agreement with the molecular formula $C_{43}H_{53}NO_6$ derived by HR FAB-MS.

Compound 2 (100 MHz): 198.1, 172.0, 162.0, 154.8, 147.1, 140.1, 138.3, 135.9, 134.0, 126.8, 122.6, 122.0, 121.8, 117.8*, 116.7, 113.2, 106.9, 76.6*, 75.3, 73.9, 73.3, 72.7, 58.2, 55.5, 49.6, 48.1, 44.5, 41.3, 39.5, 32.0, 30.4, 30.1, 30.0, 29.9, 27.8, 26.0, 24.8, 23.4, 18.0*, 17.7, 16.7, 15.3, 12.5 ppm.

The carbon count of 43 is in agreement with the molecular formula $C_{43}H_{53}NO_7$ derived by HR FAB-MS.

*Carbons marked with an asterisk were observed as broad resonances.

$^1H$ NMR Data $^1H$ NMR spectra were recorded at 300, 400 or 500 MHz spectrometers. Chemical shifts are indicated in ppm relative to TMS at zero ppm using the solvent peaks as internal standards.

Compound 1 (See FIG. 1) (500 MHz): δ0.96 (3H, s), 1.07 (3H, s), 1.12 (3H, s), 1.14 (3H, s), 1.31 (3H, s), 1.33 (3H, s), 1.42 (3H, s), ~1.46 (3H, br.s), 1.96 (3H, d, J=1 Hz), 2.32 (1H, dd, J=11, 14 Hz), 2.75 (1H, dd, J=6.5, 14 Hz), 2.81 (1H, dd, J=3, 6.0 Hz), 2.85 (1H, m), 3.43 (1H, m), 4.96 (1H, br.s), 5.09 (1H, s), 5.20 (1H, br.s), 5.22 (1H, d, J=6.0 Hz), 5.95 (1H, d, J=15 Hz), 6.06 (1H, d, J=3 Hz), 6.40 (1H, dd, J=11, 15 Hz), 7.33 (1H, br.d, J~11 Hz), 7.71 (1H, s).

Figure 2:
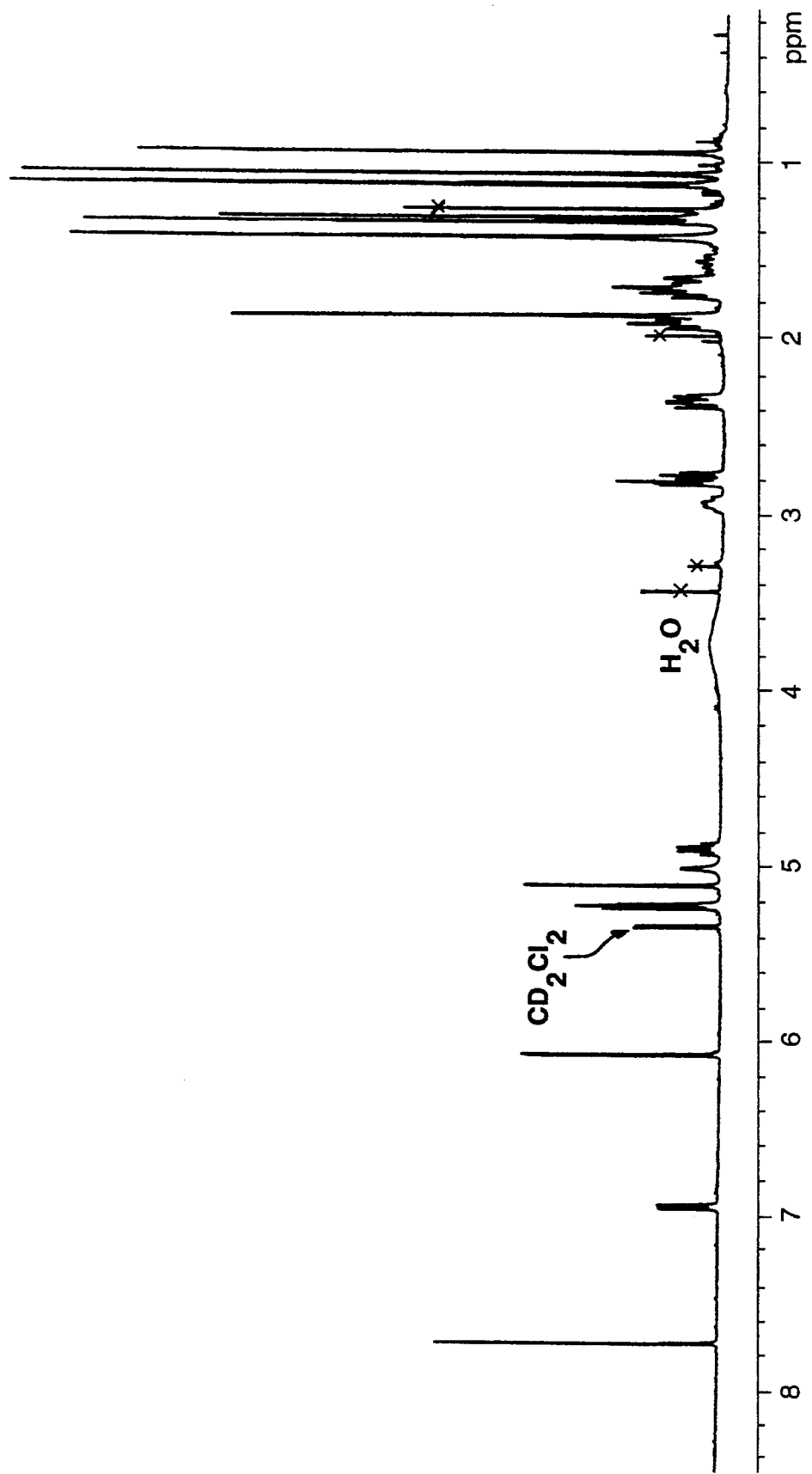

Compound 2 (See FIG. 2) (400 MHz): δ0.95 (3H, s), 1.07 (3H, s), 1.122 (3H, s), 1.126 (3H, s), 1.31 (3H, s), 1.34 (3H, s), 1.42 (6H, s), 1.73 (1H, dd, J=9.5, 12.5 Hz), 1.86 (3H, d, J=1.5 Hz), 2.34 (1H, br.dd, J=7.5, 12.5 Hz), 2.36 (1H, dd, J=11, 14 Hz), 2.78 (1H, dd, J=6.5, 14 Hz), 2.81 (1H, dd, J=3, 6.5 Hz), 2.93 (1H, m), 4.88 (H, br.q. J~8 Hz), 5.00 (1H, br.s), 5.10 (1H, s), 5.20 (1H, dq, J~1 Hz), 5.21 (1H, d, J=6.5 Hz), 6.06 (1H, d, J=3 Hz), 6.93 (1H, dq, J=8, 1.5), 7.72 (1H, s).

Figure 3:
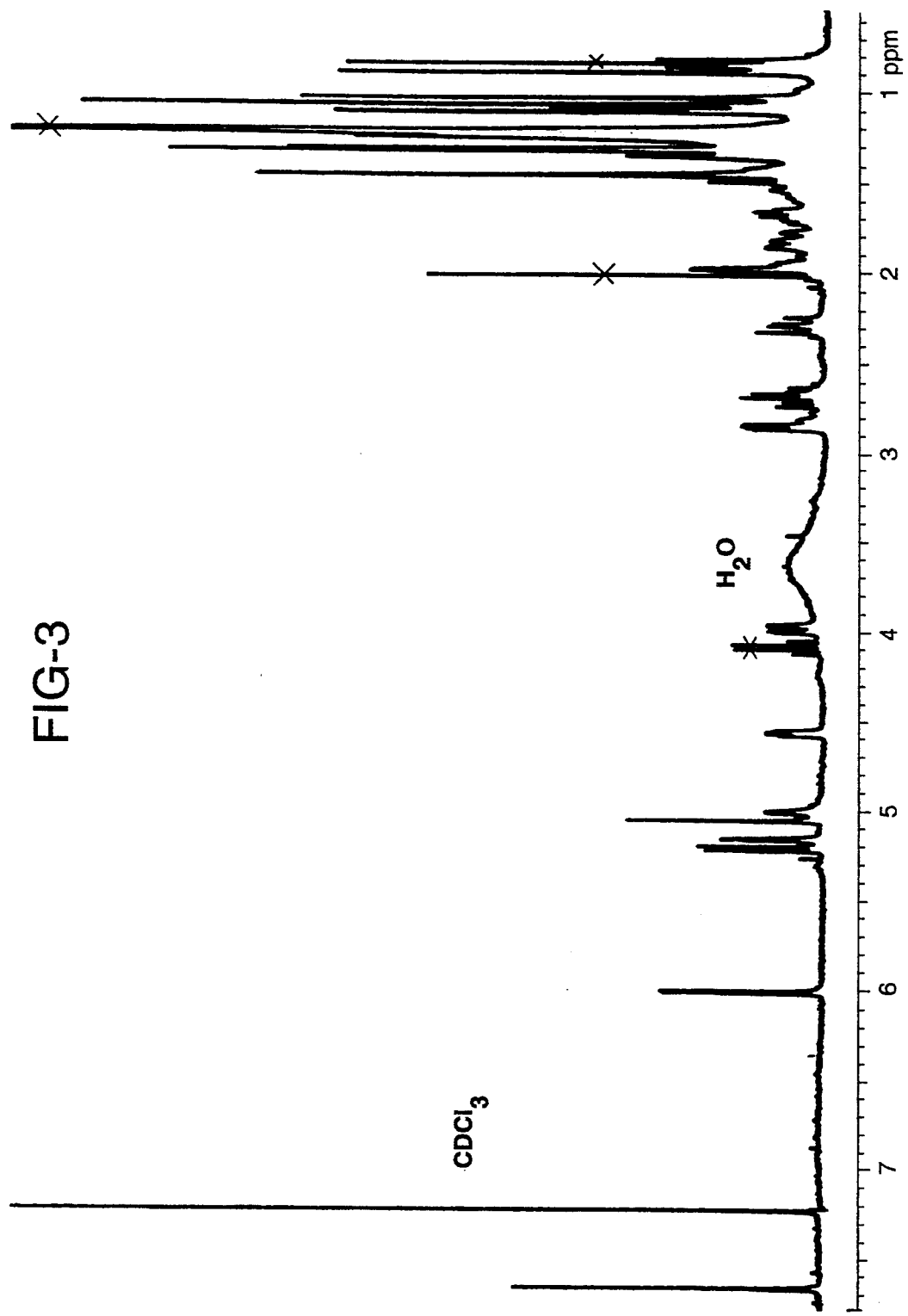

Compound 3 (See FIG. 3) (300 MHz): δ0.91 (3H, s), 1.05 (3H, s), 1.09 (3H, s), 1.11 (3H, d, J~7.5 Hz), 1.13 (3H, s), 1.33 (3H, s), 1.34 (3H, s), 1.47 (3H, s) 2.30 (1H, dd, J=10.5, 13.5 Hz), 2.72 (1H, dd, J=6.5, 13.5 Hz), 2.87 (1H, dd, J=3, 6.0 Hz), 4.00 (1H, dd, J=2.5, 10.5 Hz), 4.58 (1H, m), 5.02 (1H, br.s), 5.07 (1H, s), 5.17 (1H, br.s), 5.23 (1H, d, J=6.0 Hz), 6.02 (1H, d, J=3 Hz), 7.67 (1H, s).

Abbreviations: s=singlet, d=doublet, q=quartet, br=broad, m=multiplet, J=$^1H$—$^1H$ coupling constant in Hertz (±0.5 Hz, ~=approximately).

What is claimed is:

1. A compound having the formula:

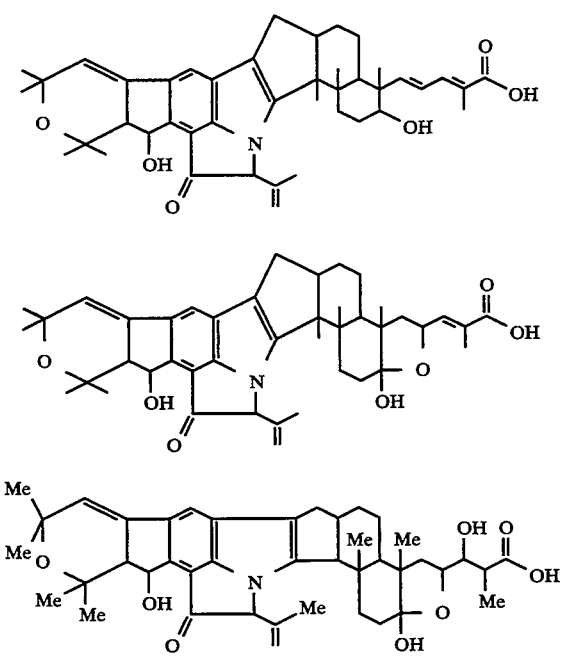

2. A composition useful for the treatment of parasitic infection of animals or plants which comprises an inert carrier and a compound of claim 1.

* * * * *

UNITED STATES PATENT AND TRADEMARK OFFICE
CERTIFICATE OF CORRECTION

PATENT NO. : 5,399,582

DATED : 3/21/95

INVENTOR(S) : Anne W. Dombrowski, Ricahrd G. Endris, Gregory L. Helms, Otto D. Hensens, John G. Ondeyka, Dan A. Ostlind, Jon D. Polishook and Deborah L. Zink It is certified that error appears in the above-identified patent and that said Letters Patent is hereby corrected as shown below:

On the title page, Item [75] : please delete "Ann W. Dombrowski, East Brunswick" and "Jon D. Polishook, Scotch Plains".

Signed and Sealed this

Tenth Day of December, 1996

Attest:

BRUCE LEHMAN

*Attesting Officer*        *Commissioner of Patents and Trademarks*